United States Patent [19]
Franz et al.

[11] Patent Number: 5,364,622
[45] Date of Patent: Nov. 15, 1994

[54] METHODS FOR PREVENTING ADHESIONS TO ORGANS AND PARTS OF ORGANS BY APPLICATION OF TISSUE PLASMINOGEN ACTIVATOR AND HYDROXYETHYLCELLULOSE HYDROGEL

[75] Inventors: Helmut Franz; Thomas Muller; Wolfgang Eisert, all of Biberach, Germany

[73] Assignee: Dr. Karl Thomae GmbH, Germany

[21] Appl. No.: 196,764

[22] Filed: Oct. 13, 1993

Related U.S. Application Data

[63] Continuation of Ser. No. 967,567, Oct. 28, 1992, abandoned, which is a continuation of Ser. No. 785,876, Nov. 4, 1991, abandoned, which is a continuation of Ser. No. 278,995, Dec. 2, 1988, abandoned.

[30] Foreign Application Priority Data

Dec. 4, 1987 [DE] Germany .............................. 3741149

[51] Int. Cl.$^5$ ........................................... A61K 37/547
[52] U.S. Cl. .................................. 424/94.64; 514/57; 424/94.3; 424/94.63; 424/488; 435/179; 435/212; 435/219
[58] Field of Search .............. 514/57; 424/94.3, 94.63, 424/94.64, 488; 435/179, 212, 219

[56] References Cited

U.S. PATENT DOCUMENTS

| | | | |
|---|---|---|---|
| 4,346,108 | 8/1982 | Singer | 424/317 |
| 4,828,836 | 5/1989 | Elger et al. | 514/54 |
| 4,889,722 | 12/1989 | Sheffield et al. | 424/450 |

FOREIGN PATENT DOCUMENTS

| | | |
|---|---|---|
| 0174835 | 3/1986 | European Pat. Off. . |
| 0227400 | 7/1987 | European Pat. Off. . |
| 0297860A1 | 1/1989 | European Pat. Off. . |
| 2119804A | 11/1983 | United Kingdom . |
| WO8400111 | 1/1984 | WIPO . |

OTHER PUBLICATIONS

Mund-Hoym, et al., *Geburtsch. u. Frauenheilk* 44:463–467 (1984), abstract.
Minju, et al., *Acta Academiae Medicinae Wuhan* 3(2):77–83 (1983), abstract.
Gazzaniga, et al., *Arch. Surg.* 110:429–432 (1975).
Holtz, *J. Reprod. Med.* 24(4): 141–146 (1980).
Rivkind, et al., *Eur. surg. Res.* 17:254–258 (1985).
Buckman, et al, *J. Surg. Res.* 20:1–5 (1976).

*Primary Examiner*—Marian Knode
*Attorney, Agent, or Firm*—Sterne, Kessler, Goldstein & Fox

[57] ABSTRACT

A method for the prevention of adhesions to body organs and parts of organs caused by therapeutic intervention by applying a pharmaceutical composition of tissue plasminogen activator and an aqueous hydroxyethylcellulose hydrogel.

16 Claims, 1 Drawing Sheet

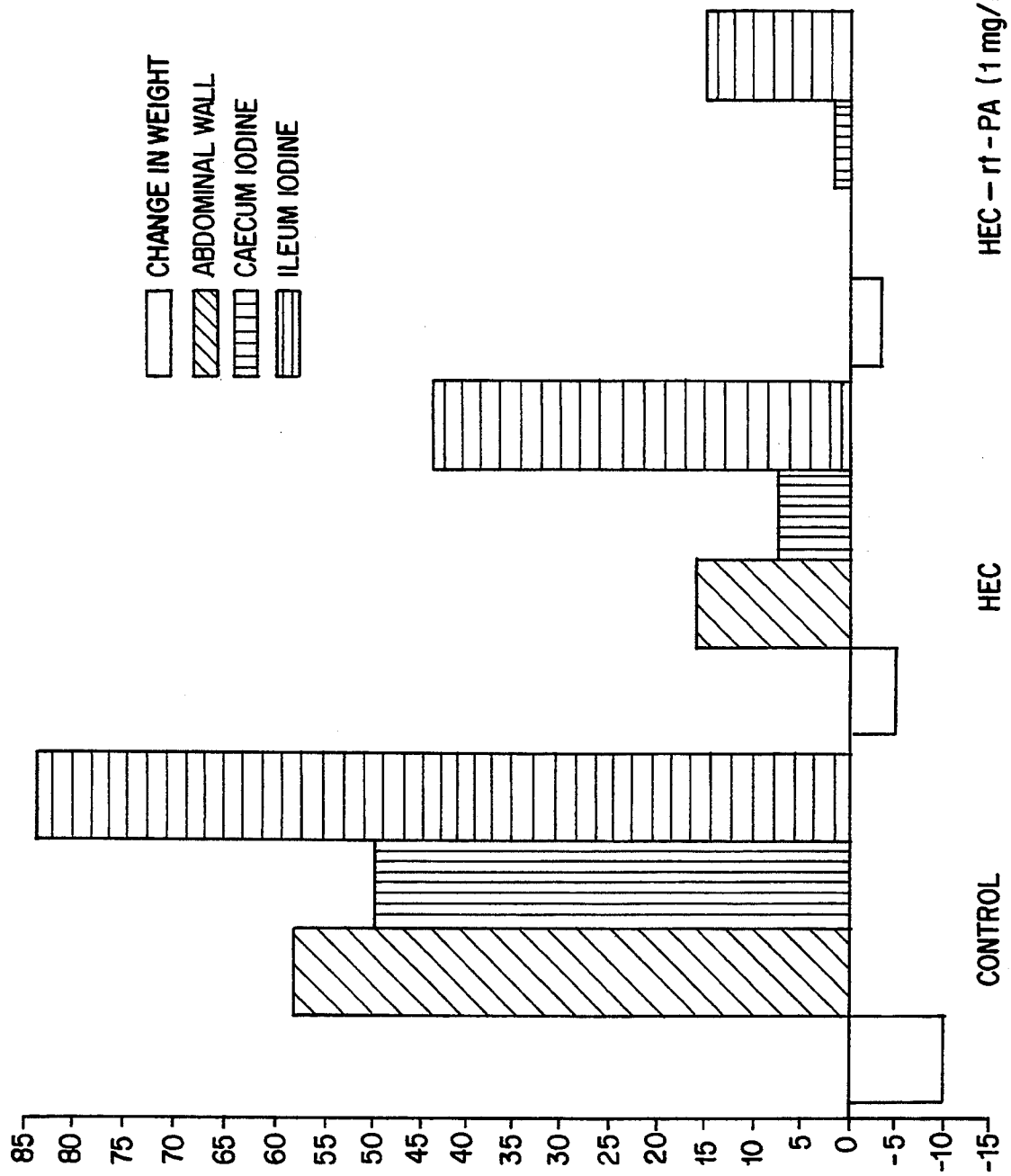

METHODS FOR PREVENTING ADHESIONS TO ORGANS AND PARTS OF ORGANS BY APPLICATION OF TISSUE PLASMINOGEN ACTIVATOR AND HYDROXYETHYLCELLULOSE HYDROGEL

This application is a continuation of application Ser. No. 07/967,567, filed Oct. 28, 1992, abandoned, which is a continuation of application Ser. No. 07/785,876, filed Nov. 4, 1991, which is a continuation of application Ser. No. 278,995 filed Dec. 2, 1988, now abandoned.

BACKGROUND OF THE INVENTION

1. Field of the Invention

The present invention relates to new methods and new preparations for preventing adhesions to body organs and/or parts of body organs.

2. Brief Description of the Background Art

After invasive therapeutic intervention or in the course of a disease, adhesions to body organs and/or parts of body organs may result in life-threatening situations. The formation of adhesions is also observed after surgical intervention in the thoracic cavities or in the abdominal cavity. In spite of greater efforts to prevent such adhesions, no satisfactory method of treatment has been discovered thus far.

The role of fibrin formation in the formation of adhesions can be explained as follows: after invasive therapeutic treatment or in inflammatory reactions, plasma proteins as well as fibrinogen and other coagulation proteins are released from the tissue. Fibrinogen is deposited in the form of fibrin. The fibrin network which forms then connects (attaches) adjacent surfaces of organs or other parts of organs. If the fibrin is not dissolved, dense adhesions are formed which may result, for example, in dangerous constrictions of the intestine. Fibrin adhesions which have been freshly formed are gradually surrounded by fibroblasts to form permanent tissue connections.

The degree of possible spontaneous fibrinolysis depends on the release of tissue plasminogen activator (t-PA) from the vascular endothelium, but also from mesothelial cells such as those which occur in the abdominal cavity. After a peritoneal intervention, however, there is a reduction in the fibrinolytic activity in these mesothelial cells. If fibrinolysis is consequently incomplete, the fibrin residues behave like centers into which fibroblasts grow. Capillaries are then formed which give rise to fibrin adhesion which are later replaced by collagen-containing adhesions, the collagen being synthesized by the fibroblasts.

To prevent the formation of post-operative or inflammation-induced adhesions, the systemic administration of ibuprofen has been proposed (U.S. Pat. No. 4,346,108); other proposals concern the parenteral administration of antihistamines, corticosteroids and antibiotics or the intraperitoneal administration of dextran solutions or polyvinylpyrrolidone solutions. The appropriate use of streptokinase, streptodornase and urokinase has also been proposed. Ascherl et al., *Medwelt* 34 (13):410–415 (1983); Mund-Hoym et al., *Geburtsb. u. Frauenheilkunde* 44:463–467 (1984); Minju et al., *Acta Academiae Medicinae Wuhan* 3(2):77–83 (1983)

Human fibrinolysin has also been investigated on its own and in conjunction with other drugs for its ability to suppress post-operative adhesions. Gazzaniga et al., *Arch. Surg.* 110:429–432 (1975) Several investigators have concluded that the post-operative formation of adhesions in the abdominal cavity is connected with a traumatically or ischaemically induced reduction in the activity of the plasminogen activator. Holtz, *The Journal of Reproductive Medicine* (4):141–146 (1980), Rivkind et al., *Eur. Surg. Res.* (Switzerland) (17)4:254–258 (1985) and Buckman et al,, *Journal of Surgical Research* 20(1):1–5 (1976).

The direct topical application of tissue plasminogen activator (t-PA) to prevent post-operative intraperitoneal adhesions was described in European Patent Application No. 0.227.400. t-PA, which occurs in the body both as a single-stranded and as a double-stranded molecule, has a high affinity for fibrin which forms clots. Natural t-PA is glycosylated and contains fatty acid residues. All these types of t-PA have a specific affinity for fibrin and at tile same time activate plasminogen to form plasmin. Plasmin effects the proteolytic breakdown of fibrin. Since fibrin is pathophysiologicatly responsible for the formation of adhesions, t-PA results in the prevention of adhesion formation and, in some cases, in the removal of adhesions already formed, e.g. in the abdominal cavity after surgical intervention or after inflammatory processes. The t-PA used is isolated from human tissue or obtained using recombinant DNA technology (GB 2.119.804 A, EP-A-0.174.835 and 0.100.982).

According to European Patent Application No. 0 227 400 mentioned above, t-PA is applied topically, for example, in the area of surgical intervention, immediately after surgery has ended if possible or before the wound has started to heal, in order to prevent adhesion of sections of tissue and/or organs. In the case of inflammatory processes, t-PA is applied to the affected areas and, if necessary, a t-PA preparation is additionally applied slowly through a catheter which ends at the site of intervention.

Sterile t-PA preparations containing a pharmaceutically acceptable carrier, e.g., a phosphate-buffered saline solution, an isotonic saline solution or purified water have also been described. Suitable organic carriers include lipids, e.g. phosphorus lipid micelles or vesicles and also dextran, polymers such as p-dioxanones, lactides and/or glycolides in the form of adsorbable polymers which are microencapsulated or embedded in ointment bases or occur in an aqueous solution of a surfactant substance, e.g., a polyoxyethylene/polyoxypropylene block copolymer or a sorbitan fatty acid ester/polyoxyethylene ether. The preferred preparations are those in which t-PA is contained in a carrier with delayed release of the active substance, which releases the active substance in controlled manner within a period from 1 to 7 days. Examples of carriers with delayed, controlled release of active substance include adsorbent polymers which occur as microcapsules or are present in an ointment base, but more particularly phospholipid vesicles, i.e., liposomes.

SUMMARY OF THE INVENTION

The present invention is based upon the inventor's discovery that post-operative and inflammation induced adhesions to body organs and/or parts of body organs may be prevented by applying a pharmaceutical composition comprising t-PA and an aqueous hydroxyethylcellulose hydrogel at the site of the operation or inflammation.

Thus, the invention relates to a new pharmaceutical composition and the use thereof in preventing adhesions to body organs and/or parts of body organs.

BRIEF DESCRIPTION OF THE FIGURE

FIG. 1. A bar graph wherein the x axis shows the extent of percentage adhesion or the percentage change in body weight for
1) the control,
2) Natrosol (HEC), 2% by weight in physiological saline solution, and
3) t-PA in Natrosol (1 mg rt-PA per ml of physiological saline solution containing 2% by weight of HEC).

BRIEF DESCRIPTION OF THE PREFERRED EMBODIMENTS

It has now been found that t-PA or rt-PA (r=recombinant), dissolved in a hydroxyethylcellulose ("HEC") gel, will prevent the formation of adhesions almost entirely, even if this hydrogel is applied only once, i.e. shortly after surgical intervention or after an inflammatory irritation on the areas with a tendency to adhesions and accretions.

The term "preventing" as used throughout this application is meant to include both avoiding the production of adhesions and removing adhesions which already exist.

The term "therapeutic intervention" is meant to include any type of therapy which is traumatic to the surrounding tissues and body organs. Examples of such therapy include surgery and endoscopy.

The term "disease process" is meant to include any physical response to a pathological condition, such as inflammation.

The term "body organs and/or parts of body organs" is intended to include any part of a living animal including but not limited to the uterus, intestines, liver, kidneys, heart and lungs.

The methods and pharmaceutical compositions of the present invention are applicable to all living animals. The preferred "subject" for the application of the invention is, however, a mammal. By the term "mammal" is meant an individual belonging to the class Mammalia. The most preferred subjects of the present invention are humans.

The term "t-PA" refers to tissue plasminogen activator and includes t-PA prepared using known conventional cell cultures of animal or human origin or by the use of known genetic engineering techniques, i.e. by known methods of DNA recombination.

The hydroxyethylcellulose to be used according to this invention is a cellulose derivative which is further described in Remington's Pharmaceutical Sciences, Mack Publishing Co., Easton, Pa. (1980), herein incorporated by reference. Hydroxyethylcellulose is commercially available under several different tradenames. The tradename of the preferred hydroxyethylcellulose of the invention is "Natrosol." It is well known in the art that hydroxyethylcellulose is produced by modifications to cellulose which consist of reactions or substitutions of cellulose's hydroxyl groups. The extent of such reactions expressed as a degree of substitution or "substitution level" of the hydroxyl groups per glucose residue. The preferred hydroxyethylcellulose of the present invention has an average molecular substitution level of from 1.5 to 3.0 hydroxyethyl groups per unit of anhydroglucose.

In order to produce a suitable pharmaceutical composition for the prevention of adhesions to body organs or parts of body organs, a microbiologically pure hydroxyethylcellulose is dissolved in water to form a hydrogel. Salts such as sodium chloride, may be added to water or to a buffer solution such as dipotassium hydrogen phosphate or sodium dihydrogen phosphate to make the pharmaceutical composition isotonic with the surrounding tissues.

The preferably lyophilised t-PA or rt-PA is dissolved in the sterilized hydrogel, and may be stored as such for several days at low temperatures. For longer storage periods, however, it is advantageous to keep the sterilized hydrogel and the lyophilised t-PA or rt-PA in separate containers and prepare the solution only just before it is required by mixing the two components together.

Tests have shown that hydroxyethyl cellulose hydrogel, alone, causes a 40 to 45% reduction in adhesions when compared with controls. The presence of t-PA causes an increase in the preventive activity of hydroxyethylcellulose hydrogel.

The pharmaceutical composition according to the invention may be administered in a variety of ways. For instance, it may be applied topically or may be readily instilled, e.g., through a channel in an endoscope, into sites which are at risk, e.g., in body cavities, if the viscosity of the preparation is reduced.

An aqueous hydrogel according to the invention comprises from 1 to 3 g of hydroxyethyl cellulose dissolved in 97 to 99 g of water or physiological saline solution and comprises 0.1 to 50 mg/ml of t-PA or rt-PA, but preferably 0.3 to 10 mg/ml with or without the addition of basic amino acids, e.g., lysine, arginine.

A preferred hydrogel comprises 1–3% by weight of hydroxyethylcellulose (e.g., Natrosol 250 HX($^R$)), dissolved in water, physiological saline or buffer solution and contains 1–2 mg/ml of t-PA or rt-PA. The most preferred hydrogel of the present invention comprises 2% by weight of hydroxyethylcellulose dissolved in a buffer solution.

A mixture of 1 mg/ml of rt-PA and 2% by weight of hydroxyethylcellulose in physiological saline solution was compared with a mixture of 2% by weight of hydroxyethylcellulose in physiological saline solution and with controls (using only physiological saline or buffer solution) in rabbits. Adhesions were produced in two ways: (a) by applying stitches to the abdominal wall after laparotomy and (b) by irritating the peritoneal tissue in the region of the caecum, ileum and the small pelvis with an iodine solution.

When stitches were inserted in the abdominal wall after laparotomy, the test substance was applied and the laparotomy incision was closed up in several layers. The operating surgeon or investigator was not aware of the composition of the test substance. After 1 week, in a large section of skin, the area of the old laparotomy incision was cut and folded open, the length of intestinal tissue adhering to the laparotomy incision was measured and the length which had adhered was expressed as a percentage of the length of the laparotomy incision.

During the laparotomy, the test substance (with and without t-PA) was applied immediately after the irritation of the caecum, ileum and small pelvis with iodine and before the abdominal cavity had been closed up. Once again, the surgeon was not aware of the composition of the test substance.

One week after the first laparotomy, the animals were again subjected under anesthesia to laparotomy to determine the extent of the adhesions. The area of firm adhesions in the treated sections of intestine in the damaged areas was measured. The results are shown in FIG. 1 as the percentage adhesion, based on the area of damage. In addition, the body weight of the animals was determined on the day of the original laparotomy and the second laparotomy.

A comparison of the results presented in FIG. 1 shows that hydroxyethylcellulose hydrogel on its own brought about, on average, a 40 to 45% reduction (based on the controls) in the adhesions induced by the conditions, in the caecum and ileum, but in conjunction with rt-PA there was an almost total (95%) reduction in the caecum and a reduction of approximately 85% in the ileum. As for the adhesion of the laparotomy incision (abdominal wall) with the underlying tissue, hydrogel on its own results in a substantial reduction; however, the presence of rt-PA prevents adhesion completely.

The use of the hydrogel preparations according to the invention containing t-PA and rt-PA significantly minimizes the loss of body weight during the first stage of healing.

Having now generally described the invention, a more complete understanding can be obtained by reference to the following specific examples. These examples are provided for purposes of illustration only and are not intended to be limiting unless otherwise specified.

EXAMPLE 1 rt-PA Set Containing 0.1 mg rt-PA/ml

1) In a suitable container, 2 g of microbiologically pure hydroxyethylcellulose are sprinkled into 98 g of sterile-filtered physiological saline solution and dissolved therein with stirring at ambient temperature. The gel formed is transferred, under laminar air flow, into 50 ml vials with insertable caps, then sealed with rubber stoppers and flanged, then sterilized for 30 minutes at 121° C. in pressurized steam. The sealed gel can be stored for two years at ambient temperature.

2) rt-PA is lyophilised in quantities of 10, 20 and 30 mg under sterile conditions in vials provided with insertable caps, then sealed with rubber stoppers and flanged. The sealed vial can be stored for up to two years at ambient temperature (up to 25° C.).

3) Solution ready for use: 5 mg of lyophilised rt-PA are introduced, under laminar air flow conditions, into 50 g of sterile 2% by weight hydroxyethylcellulose gel and dissolved therein with stirring using a sterile glass rod.

This gel which is ready for use may either be applied to the stitches in the wound immediately or may be stored for a few days at 4° C. in a refrigerator.

EXAMPLE 2 rt-PA Gel Containing 1.0 mg of rt-PA/ml

Before use, 50 mg of lyophilised rt-PA are introduced into 50 g of sterile, 2% by weight hydroxyethylcellulose gel which has been made isotonic and is dissolved therein by stirring with a sterile glass rod.

The gel ready for use may be stored for a few days in the refrigerator.

EXAMPLE 3

(rt-PA Gel Containing 10.0 mg of rt-PA/ml)

Before use, 500 mg of lyophilised rt-PA are introduced into 50 g of sterile, 2% by weight hydroxyethylcellulose gel which has been made isotonic.

The finished gel may be stored for a few days in the refrigerator.

We claim:

1. A method of preventing adhesions to body organs and/or parts of body organs caused by therapeutic intervention comprising applying to a subject a pharmaceutical composition comprising natural or recombinant t-PA, and
an aqueous hydroxyethyl cellulose hydrogel wherein said pharmaceutical composition is applied at the site of said intervention in an amount effective to prevent said adhesions.

2. The method of preventing adhesions of claim 1, wherein said body organs and/or said body organ parts are in a body cavity.

3. The method of preventing adhesions of claim 2, wherein said body cavity is a thoracic cavity.

4. The method of preventing adhesions of claim 2, wherein said body cavity is an abdominal cavity.

5. The method of preventing adhesions of claim 1, wherein said therapeutic intervention is invasive.

6. The method of preventing adhesions of claim 5, wherein said invasive therapeutic intervention is surgery.

7. The method of preventing adhesions of claim 1, wherein said subject is a mammal.

8. The method of preventing adhesions of claim 7, wherein said mammal is a human.

9. The method of preventing adhesions of claim 1, wherein said application is topical.

10. The method of preventing adhesions of claim 1, wherein said application is by instillation through a tube.

11. The method of preventing adhesions of claim 1, wherein said pharmaceutical composition further comprises an isotonic solution.

12. The method of preventing adhesions of claim 1, wherein said pharmaceutical composition further comprises a buffer solution.

13. The method of preventing adhesions of claim 1, wherein said pharmaceutical composition comprises of 0.1 to 50 mg/ml of natural or recombinant t-PA and said hydrogel comprises 1 to 3% by weight of hydroxyethylcellulose in aqueous solution.

14. The method of preventing adhesions of claim 13, wherein said pharmaceutical composition comprises 0.3 to 10 mg/ml of natural or recombinant t-PA.

15. The method of preventing adhesions of claim 13 wherein said pharmaceutical composition comprises 1 to 2 mg/ml of recombinant t-PA and said hydrogel comprises 1 to 3% by weight of hydroxyethylcellulose in a buffer solution.

16. The method of preventing adhesions of claim 1, wherein said hydrogel comprises hydroxyethylethers of cellulose having an average molecular substitution level of from 1.5 to 3.0 hydroxyethyl groups per unit of anhydroglucose.

* * * * *